United States Patent [19]

Livingston et al.

[11] Patent Number: 5,102,663

[45] Date of Patent: Apr. 7, 1992

[54] VACCINE FOR STIMULATING OR ENHANCING PRODUCTION OF ANTIBODIES AGAINST 9-O-ACETYL GD3

[75] Inventors: Philip O. Livingston; Gerd J. Ritter, both of New York, N.Y.; Herbert F. Oettgen, New Canaan, Conn.; Lloyd J. Old, New York, N.Y.

[73] Assignee: Sloan-Kettering Instutute for Cancer Research, New York, N.Y.

[21] Appl. No.: 259,182

[22] Filed: Oct. 18, 1988

[51] Int. Cl.$^5$ .................. A61K 39/39; A61K 37/20; A61K 37/22; A61K 39/395

[52] U.S. Cl. ................. 424/88; 424/85.8; 424/422; 424/423; 514/25; 514/885; 530/806; 530/842; 530/387.5; 530/389.7; 436/23; 436/503; 436/813; 436/822; 436/823

[58] Field of Search ............. 424/88, 85.8, 422, 423; 514/25, 885; 530/387, 806, 842; 436/23, 503, 813, 822, 823

[56] References Cited

U.S. PATENT DOCUMENTS

4,849,509  7/1989  Thurin et al. ............... 530/387
4,918,164  4/1990  Hellstrom et al. ........... 530/387

OTHER PUBLICATIONS

Cheresh, D. A. et al., J. Biol. Chem. 12:7453-7459, 1984.
Pinsky, C. M. et al., Rec. Results Cancer Res. 47:37-41, 1974.
Haverkamp, J. et al., Hoppe-Seyler's Z. Physiol. Chem. 356:1575-1583.
Momoi, T. et al., Hoppe-Seyler's Z. Physiol. Chem. 361:1201-1210.
H. Towbin et al., (1984) Journal of Immunological Methods, 72:471-479.
R. W. Ledeen et al., (1973) Journal of Neurochemistry, 21:829-839.
Tadashi Tai, (1985) *Int. J. Cancer*, 35:607-612.
Leslie D. Cahan et al., (1982) Proc. Natl. Acad. Sci., 79:7629-7633.
Roland Schauer (1978) Characterization of Sialic Acids. In. V. Ginsburg (ed.), *Methods of Enzymology*, vol. L., part C:64-89.
Hiroshi Yamaguchi et al., (1987) Proc. Natl. Acad. Sci., 84:2416-2420.
Makoto Ito and Tatsuya Yamagata (1986) Journal of Biological Chemistry, 261(30): 14278.
Philip O. Livingston et al., (1987) The Journal of Immunology, 138(5): 1524.
Nai-Kong V. Cheung et al., (1986) Journal of Clinical Oncology, 5(9):1430.
Philip O. Livingston et al., (1986) Proc. Natl. Acad. Sci. U.S.A. 84:2911.
Alan N. Houghton et al., (1985) Proc. Natl. Acad. Sci. U.S.A. 82:1242.
Reiko F. Irie and Donald L. Morton (1986) Proc. Natl. Acad. Sci. U.S.A. 83:8694.
Andrew S. Blum et al., (1987) Proc. Natl. Acad. Scie. U.S.A. 84:8716-8720.
Tetsuya Tsuchida et al., (1987) JNCI 78(1): 45-50.
Tetsuya Tsuchida et al., (1987) JNCI 78(1) 55-60.
Wolfgang G. Dippold et al., (1980) Proc. Natl. Acad. Sci. U.S.A. 70(10): 6114-6118.
Robert K. Yu et al., (1985) J. Biochem. 98:1367-1373.
Su-Chen Li et al., (1975) Journal of Biological Chemistry, 250(17): 6786-6791, 1975.

(List continued on next page.)

*Primary Examiner*—Thurman K. Page
*Assistant Examiner*—Carlos Azpuru
*Attorney, Agent, or Firm*—John P. White

[57] ABSTRACT

The present invention provides a vaccine for stimulating or enhancing in a subject to whom the vaccine is administered, production of antibodies directed against 9-O-acetyl GD3 ganglioside comprising an amount of purified 9-O-acetyl GD3 ganglioside effective to stimulate or enhance antibody production in the subject and a pharmaceutically acceptable carrier. This invention also provides purified ganglioside and ganglioside mixtures which comprise 9-O-acetyl GD3 ganglioside and one or more additional acetyl groups.

22 Claims, 9 Drawing Sheets

OTHER PUBLICATIONS

Alan N. Houghton et al., (1983) J. Exp. Med. 158: 53–65.

Philip O. Livingston et al., (1982) Int. J. Cancer 30:413–422.

Giuliano Gazzotti et al., (1985) Journal of Chromatography, 348: 371–378.

Rudiger W. Veh et al., (1981) Journal of Chromotography, 212: 313–322.

Hideo Kubo et al., (1985) Journal of Lipid Research 26: 638–641.

Philip O. Livingston et al., (1985) The Journal of Immunology, 135:2.

Herb Ritter, Walter Krause, Rudolf Geyer, Stephan Stirm, Herbert Wiegandt: Archives of Biochemistry and Biophysics, 257(2): 370–378.

Jacquess Portoukalian, Georges Zwinglestein and Jean-Francois Dore (2979) Eur. J. Biochem., 94: 19–23.

Lloyd J. Old (1981) Cancer Research 41: 361–375.

John L. Magnani et al., (1980) Analytica Biochemistry, 109:399–402.

Edward J. Natoli, Jr. et al., (1986) Cancer Research 46: 4116–4120.

Kazuo Nakamura et al., (1984) Analytic Biochemistry, 152:406–410.

Francisco X. Real et al., (1985) Cancer Research 45: 4401–4411.

Livingston, P. O. et al., (1983) Int. J. Cancer 31:567–575.

Cheresh, D. A. et al., (1984) Science 225: 844–846.

Ravindranaths, M. H. et al., (1988) J. Biol. Chem. 263: 2079–2086.

Thurin, J. et al., (1985) J. Biol. Chem. 260: 14556–14563.

O-acetylation of GD3 monitored by HPTLC

Preparative separation of 0-acetyl-GD3 derivatives by HPLC
($NH_2$-col; acetonitrile/phosphate buffer gradient)

HPTLC of Isolated O-acetyl-GD3 derivatives

ITLC of 0-acetyl-GD3 derivatives

Partial 490 MH$_z$ $^1$H-NMR spectrum
of F2 in DMSO-d$_6$/D$_2$O at 303°K (4.5-4.0 ppm)

VACCINE FOR STIMULATING OR ENHANCING PRODUCTION OF ANTIBODIES AGAINST 9-O-ACETYL GD3

This invention was made with government support under Grant Numbers CA-40532 and CA-43971, National Cancer Institute, Department of Health and Human Services. Accordingly, the U.S. Government has certain rights in the invention.

BACKGROUND OF THE INVENTION

Throughout this application, various publications are referenced by arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed in this application.

Gangliosides are prominent cell-membrane components of melanoma and other tumors of neuroectodermal origin. Many different gangliosides have been described in melanoma cells. These include GM3, GM2, GMI, GD3, GD1A, GD1B, GD2, GT1B, 9-0 acetyl GD3, and GT3 (1-2). Four of these, GM2, GD2, GD3, and 9-0 acetyl GD3, have attracted special attention because of wide distribution on melanoma cells and limited distribution on cells outside the central nervous system (3-6). The importance of GD2 and GD3 has been suggested by regression of melanoma and neuroblastoma metastases in some patients treated with anti-GD3 and anti-GD2 monoclonal antibodies (MmAb) (7-9). Many patients have received vaccines containing melanoma cells expressing these gangliosides (10-13). These studies have shown that GM2 antibodies were frequently induced, antibodies against GD2 were occasionally induced, and antibodies against GD3 and 9-0 acetyl GD3 were never detected. Due to uncertainties about expression of each ganglioside in the vaccines, or on the target cells used for serological analysis, the relative immunogenicity of GM2, GD2, GD3 and 9-0 acetyl GD3 remained unknown.

In attempts to induce active immunity against melanoma, we focused on GM2 in initial studies because its distribution on cell lines (defined by anti-GM2 MmAb 5.3) and on various tissues (detected by extraction and thin layer chromatography) was quite restricted (3). In a series of experiments in the mouse, we have identified immunizing procedures that facilitate the serologic response to GM2 and other gangliosides (14-15): pretreatment with low dose cyclophosphamide and immunization with GM2 attached to adjuvant-carriers such as BCG or *Salmonella minnesota* mutant R595. Trials comparing these approaches in early stage melanoma patients demonstrated BCG to be a significantly better adjuvant than R595 and patients pretreated with a low dose of cyclophosphamide had significantly higher titers of anti-GM2 antibody than those not receiving this pretreatment (12). IgM antibodies were induced in 72% of patients receiving the BCG-GM2 vaccine, and these were capable of lysing human tumor cells in the presence of human complement. IgG antibodies were detected in 25% of the immunized patients. The pattern of primary and secondary antibody response to immunization was most consistent with GM2 acting as a T cell independent antigen.

In the study reported here, we apply the same immunization approach, CY +BCG - purified ganglioside, to test the immunogencity of GD2, GD3, and 9-acetyl GD3. The relative immunogenicity of these gangliosides was examined in AJCC stage III and IV melanoma patients who were free of detectable disease after surgery. 9-0-acetyl GD3 is identified as a second effective immunogen.

Nothing yet is known about the immunogenicity of 0-acetyl-GD3. Although structually close to GD3, the molecule is antigenically different (5,6 16-17). While Ravindranaths et al. have recently described 2 melanoma patients with antib-ody reactivity against 9-0-acetyl and/or 4-0 acetyl GD3, the incidence of such antibodies in melanoma patients was unknown (18). In this study we report our attempts at chemically synthesizing 0-acetyl-GD3 and characterizing the properties of the products obtained. As immunization of patients with malignant melanoma with these derivatives is envisaged, we examined their immunogenicity in the mouse, by analysing the humoral immune response after vaccination with 0-acetyl-GD3 derivatives.

SUMMARY OF THE INVENTION

This invention provides vaccine for stimulating or enhancing in a subject to whom the melanoma vaccine is administered, production of antibodies against 9-0-acetyl GD3 ganglioside comprising an amount of a 9-0-acetyl GD3 ganglioside effective to stimulate or enhance antibody production in the subject and a pharmaceutically acceptable carrier.

This invention further provides the aforementioned melanoma vaccine which additionally comprises an adjuvant. In accordance with the teachings of this invention, the adjuvant may be a microbial adjuvant. This microbial adjuvant may further comprise *Salmonella minnesota* R595 or bacillus Calmette-Guerin.

This invention also provides the aforementioned melanoma vaccine wherein the effective amount of 9-0-acetyl GD3 ganglioside comprises an amount between about 50 micrograms and about 300 micrograms.

Additionally, this invention also provides the aforementioned melanoma vaccine wherein the 9-0-acetyl GD3 ganglioside is purified from a biological source. In accordance with the teachings of this invention the biological source may be melanoma cells, milk or buttermilk.

This invention also provides the aforementioned melanoma vaccine which additionally comprises purified GM2 ganglioside.

Furthermore, this invention also provides the aforementioned melanoma vaccines wherein the subject is afflicted with cancer and the antibody produced in the subject upon administration of the melanoma vaccine effectively treats the cancer. Additionally provided are the aforementioned melanoma vaccines wherein the subject is susceptible to cancer and the antibody produced in the subject upon administration of the melanoma vaccine effectively prevents the cancer. In accordance with the teachings of this invention, the cancer is of neuroectodermal origin, and the cancer of neuroectodermal origin may be a melanoma.

This invention further provides a method for stimulating or enhancing in a subject production of antibodies against 9-0-acetyl GD3 ganglioside comprising administering to the subject an effective dose of the aforementioned melanoma vaccines.

Additionally, this invention provides a method for treating cancer and a method for preventing cancer in a subject affected with cancer comprising administering to the subject an effective dose of the aforementioned melanoma vaccines. In accordance with the teachings of this invention, 9-0-acetyl GD3 ganglioside of the aforementioned melanoma vaccine methods may be bound to a microbial adjuvant. Furthermore, the 9-0-acetyl GD3 ganglioside may be bound to the microbial adjuvant by a hydrophobic bond between the lipid portion of the 9-0-acetyl GD3 ganglioside and the cell membrane of the microbial adjuvant and the microbial adjuvant may be *Salmonella minnesota* R595 or bacillus Calmette-Guerin.

This invention additionally provides that in the aforementioned melanoma vaccine methods, the cancer may be of neuroectodermal origin, and the cancer of neuroectodermal origin may be a melanoma. Furthermore, in the aforementioned melanoma vaccine methods, an effective amount of cyclophosphamide may be administered to the subject prior to administering the melanoma vaccine, and the cyclophosphamide also may be administered between about 3 days and about 7 days prior to the administering the melanoma vaccine. Also in accordance with the teachings of this invention, the effective amount of cyclophosphamide may be between about 1 mg/m$^2$ and about 500 mg/m$^2$.

This invention additionally provides a 9-0-acetyl GD3 ganglioside designated F2 characterized by the presence of a second acetyl group and the mass spectra show in FIGS. 6A, 6B, and 6C. Also provided is a 9-0-acetyl GD3 ganglioside designated F3 characterized by the presence of 2 or more additional acetyl groups and recoverable from a mixture of acetylated derivatives of GD3 by a high pressure liquid chromatography. Further, the invention provides for a mixture of the 9-0-acetyl GD3 gangliosides F2 and F3.

Finally, the invention provides a melanoma vaccine for stimulating or enhancing in a subject to whom the melanoma vaccine is administered, production of antibodies against 9-0-acetyl GD3 ganglioside comprising an amount of a 9-0-acetyl GD3 ganglioside of any of F2 or F3 ganglioside or mixture thereof effective to stimulate or enhance antibody production in the subject and a pharmaceutically acceptable carrier.

DETAILED DESCRIPTION OF THE INVENTION

Figure 1:
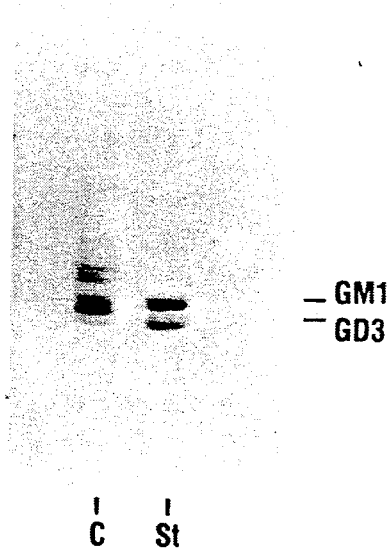
FIG. 1 shows the migration of 0-acetylated derivatives of GD3 in TLC. C, 0-acetylated GD3; St, reference gangliosides GM1 and GD3; HPTLC silica gel plate; running solvent: chloroform/methanol/0.2% aqueous CaCl$_2$ 60:35:8 v/v; spray reagent: orcinol/H$_2$SO$_4$.

This invention provides a melanoma vaccine for stimulating or enhancing in a subject to whom the vaccine is administered, production of antibodies against 9-0-acetyl GD3 ganglioside comprising an amount of a 9-0-acetyl GD3 ganglioside effective to stimulate or enhance antibody production in the subject and a pharmaceutically acceptable carrier.

As used herein, the term "pharmaceutically acceptable carrier" encompasses any of the standard pharmaceutical carriers such as a phosphate buffered saline solution, water, emulsions such as oil/water emulsion, and various types of wetting agents.

In this method, the administration of the compound may be effected by any of the well known methods, including but not limited to intravenous, intramuscular, and subcutaneous administration.

This invention further provides the aforementioned melanoma vaccine which additionally comprises an adjuvant. In accordance with the teachings of this invention, the adjuvant may be a microbial adjuvant. This microbial adjuvant may further comprise *Salmonella minnesota* R595 or bacillus Calmette-Guerin.

A range of the amount of *Salmonella minnesota* R595 may be employed. However, the preferred amount present in the vaccine is an amount between about 0.2 mg and about 1.5 mg. Further, a range of the amount of bacillus Calmette-Guerin may be employed. However, the preferred amount present in the vaccine is an amount between about $10^5$ viable units and about $3 \times 10^7$ viable units.

This invention also provides the aforementioned melanoma vaccine wherein the effective amount of 9-0-acetyl GD3 ganglioside comprises an amount between about 50 micrograms and about 300 micrograms.

Additionally, this invention also provides the aforementioned melanoma vaccine wherein the 9-0-acetyl GD3 ganglioside is purified from a biological source. In accordance with the teachings of this invention the biological source may be melanoma cells, milk or buttermilk.

This invention also provides the aforementioned melanoma vaccine which additionally comprises purified GM2 ganglioside.

Furthermore, this invention also provides the aforementioned melanoma vaccines wherein the subject is afflicted with cancer and the antibody produced in the subject upon administration of the vaccine effectively treats the cancer. Additionally provided are the aforementioned melanoma vaccines wherein the subject is susceptible to cancer and the antibody produced in the subject upon administration of the vaccine effectively prevents the cancer. In accordance with the teachings of this invention, the cancer is of neuroectodermal origin, and the cancer of neuroectodermal origin may be a melanoma.

This invention further provides a method for stimulating or enhancing in a subject production of antibodies against 9-0-acetyl GD3 ganglioside comprising administering to the subject an effective dose of the aforementioned melanoma vaccines.

Additionally, this invention provides a method for treating cancer and a method for preventing cancer in a subject affected with cancer comprising administering to the subject an effective dose of the aforementioned melanoma vaccines. In accordance with the teachings of this invention, 9-0-acetyl GD3 ganglioside of the aforementioned melanoma vaccine methods may be bound to a microbial adjuvant. Furthermore, the 9-0-acetyl GD3 ganglioside may be bound to the microbial adjuvant by a hydrophobic bond between the lipid portion of the 9-0-acetyl GD3 ganglioside and the cell membrane of the microbial adjuvant and the microbial adjuvant may be Salmonella minnesota R595 or bacillus Calmette-Guerin. In the case of the melanoma vaccine which additionally comprises purified GM2 ganglioside, either the 9-0-acetyl GD3 or GM2 ganglioside may be bound to the adjuvant.

This invention additionally provides that in the aforementioned melanoma vaccine methods, the cancer may be of neuroectodermal origin, and the cancer of neuroectodermal origin may be a melanoma. Furthermore, in the aforementioned melanoma vaccine methods, an effective amount of cyclophosphamide may be administered to the subject prior to administering the melanoma vaccine, and the cyclophosphamide also may be administered between about 3 days and about 7 days prior to the administering the vaccine. Also in accordance with the teachings of this invention, the effective amount of cyclophosphamide may be between about 1 mg/m$^2$ and about 500 mg/m$^2$.

Figure 6A:
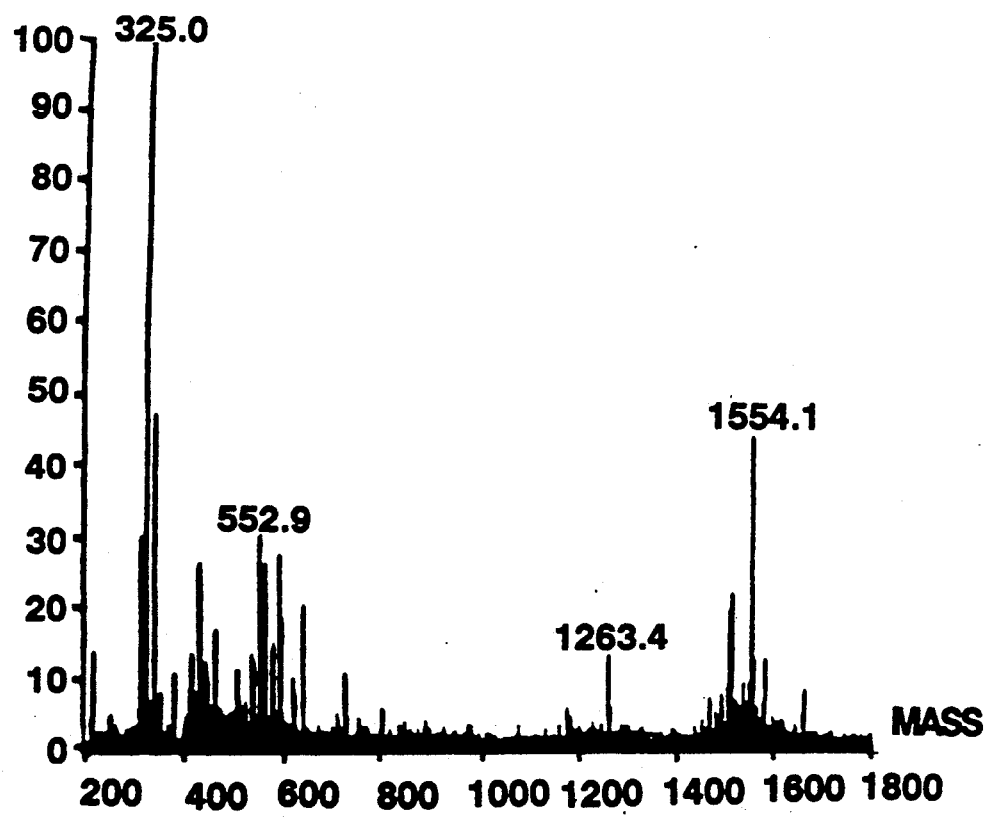
FIG. 6 shows the FAB-ME spectra of fraction F2.
A: complete spectrum;
B: partially extended spectrum mass range 1400–1600; and
C: partially extended spectrum mass range 400–800.
Figure 6B:
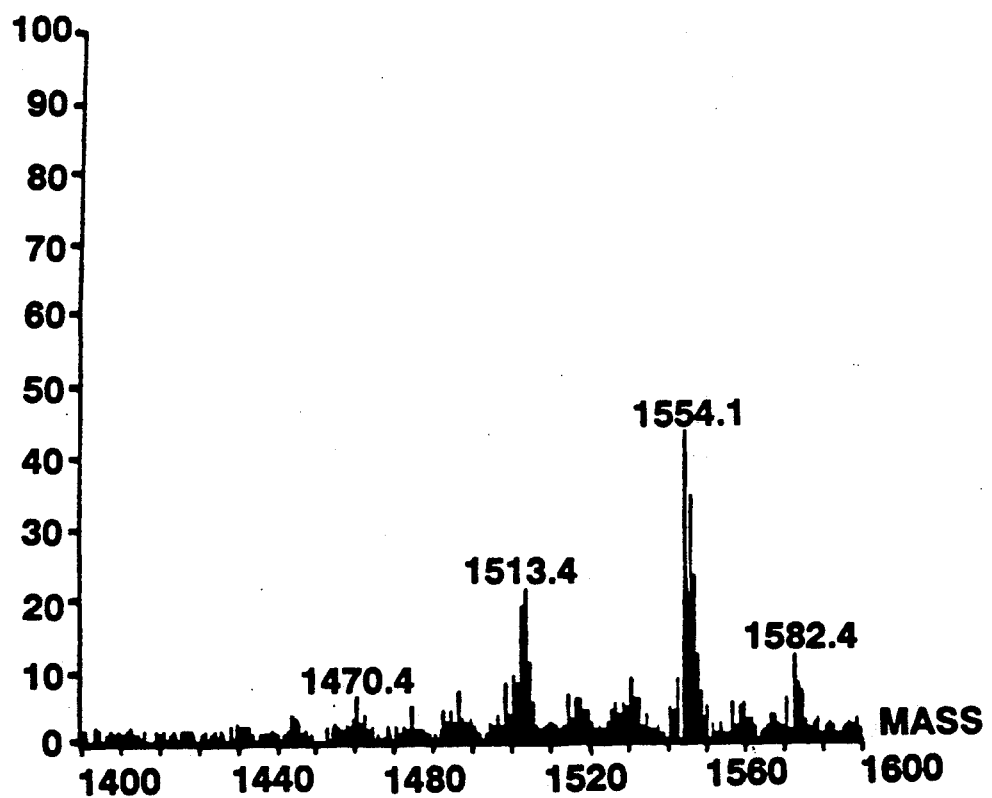
Figure 6C:
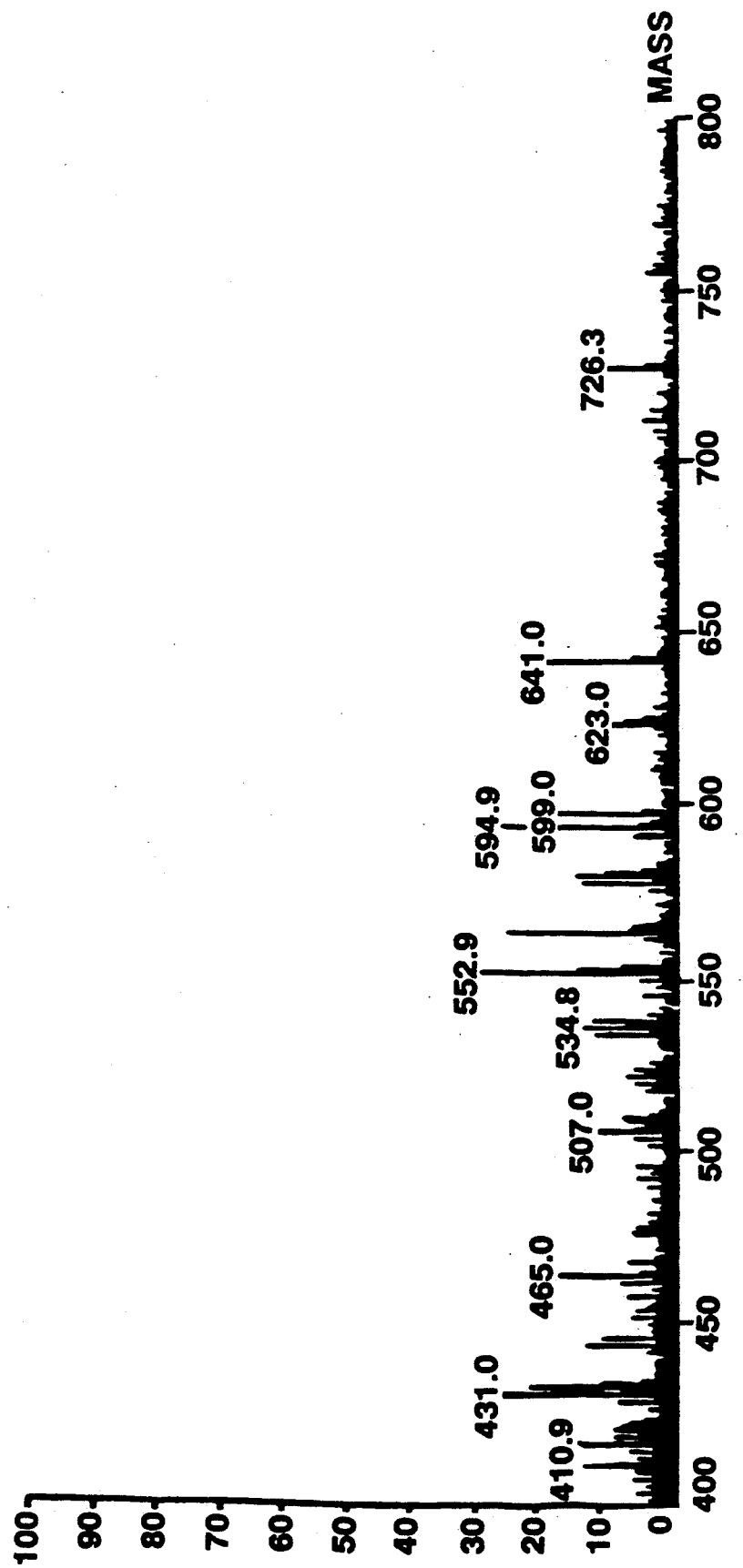

This invention additionally provides a 9-0-acetyl GD3 ganglioside designated F2 characterized by the presence of a second acetyl group and the mass spectra show in FIGS. 6A, 6B, and 6C. Also provided is a 9-0-acetyl GD3 ganglioside designated F3 characterized by the presence of 2 or more additional acetyl groups and recoverable from a mixture of acetylated derivatives of GD3 by a high pressure liquid chromatography. Further, the invention provides for a mixture of the 9-0-acetyl GD3 gangliosides F2 and F3.

Finally, the invention provides a melanoma vaccine for stimulating or enhancing in a subject to whom the vaccine is administered, production of antibodies against 9-0-acetyl GD3 ganglioside comprising an amount of a 9-0-acetyl GD3 ganglioside of any of F2 or F3 ganglioside or mixture thereof effective to stimulate or enhance antibody production in the subject and a pharmaceutically acceptable carrier.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Materials and Methods

Patients. Melanoma patients with regional skin and lymph node metastases or systemic metastases were considered eligible if tumors had been resected within four months and if they were free of detectable melanoma. None of the patients had received chemotherapy or radiation therapy within eight weeks. Patients were examined at six-week intervals. Chest x-rays, liver function tests, and urinalysis were performed at three-month intervals. Blood for serologic tests was obtained at two-week intervals.

Gangliosides. GM2 and GD2 were prepared by treating GM1 and GD1B with β-galactosidase (G. W. Jourdian, University of Michigan, Ann Arbor, Mich.) according to published methods (19). GM1, GD1A, and GT1 were purchased from Supelco (Bellafonte, PA). GD1B was purchased and GD3 (for conversion to 9-0 acetyl GD3) was kindly supplied as a gift by Fidia Research Labs, Abano Terme, Italy. 9-0-acetyl GD3 was prepared by acetylation of GD3 as previously described. GM3 and GD3 (for GD3 vaccines) were purified from dog erythrocytes and human melanoma respectively as previously described (3).

Serological Procedures. The enzyme-linked immunosorbent assay (ELISA) was performed with rabbit anti-human IgM, anti-human IgG, or protein A conjugated to alkaline phosphatase (Zymed Laboratories, San Francisco) (12). Normal or pretreatment sera served as blanks and were subtracted from experimental values. Antibody titer was defined as the highest serum dilution yielding a corrected OD >0.190. Reagents for dot blot immune stains were peroxidase conjugated goat anti human IgM and goat antihuman IgG (Tage, Burlingame, CA) diluted 1:500. Dot blots were graded as negative, 1+, 2+ or 3. Complement dependent cytotoxicity assays were performed with normal human serum (diluted 1:3) as the complement source as previously described (11).

Skin Tests for Delayed Hypersensitivity (DTH). Six, 12, and 25 mg of the immunizing ganglioside was suspended in 0.05 ml normal saline and injected intradermally. Skin tests for DTH against mumps and other recall antigens were performed and interpreted as previously described (20).

Ganglioside Vaccines. $10^7$ viable units of BCG (Tice strain, University of Illinois), or $3 \times 10^6$ units in the case of patients showing strong reactions to BCG, were suspended in distilled water by sonication and added to tubes containing 50 mg of 9-0 acetyl GD3, 100, 200 or 300 μg of GM2, 200 μg of GD2, 300 μg of GD3, or 200 μg of GM2, GD2 and GD3. The suspension was lyophilized and suspended in PBS shortly before vaccine administration. Patients received three vaccinations intradermally at two-week intervals on a rotating basis to uninvolved extremities. In addition, a booster immunization was administered two months after the third vaccination.

Cyclophosphamide Administration. Cy (Cytoxan, Mead Johnson and Co., Evansville, Ind.) 200 mg/M was administered to all patients IV four to six days prior to the initial immunization.

Glycolipids and chemicals: GM3, GM2 and GMI gangliosides were purchased from, and GD3 was generously provided by Fidia Research Laboratories (Abanc Terme, Italy); neutral glycosphingolipids were prepared from human spleen in our laboratory by published procedures (21); HPTLC silica gel plates were obtained from E. Merck (Darmstadt, FRG); Nitrocellulose membranes (0.2 μm) were obtained from Schleicher and Schuell, Inc. (Keene, NH); Preparative (21.4×250 mm) and semi-preparative (10×250 mm) aminopropyl and C18 HPLC-columns were obtained from Rainin Instruments Co. (Ridgefield, N.J.); analytical (3.9×300 mm) aminopropyl HPLC-column and Sep-Pak C18-cartridges were obtained from Waters Associates (Milford, Mass.); DEAE-Sephadex A25 4-chloro-1-naphthol, p-nitrophenyl phosphate disodium, sodium-taurodeoxycholate and N-acetyl-imidazole were obtained from Sigma Chemical Co. (St. Louis, Mo.). Cyclophosphamide (Cytoxan) was obtained from Mead Johnson (Syracuse, N.Y.).

Enzymes. Endoglycoseramidase was kindly provided by Dr. Makoto Ito from the Mitsubishi-Kasei Institute of Life Science (Tokyo, Japan); $V.$ cholerae sialidase (E.C. 1.2.1.13) Was obtained from Calbiochem-Behring Corporation (La Jolla, CA). Jack bean β-galactosidase (E.C. 3.2.1.23) was obtained from Sigma Chemical Co. (St. Louis, Mo.).

Monoclonal antibodies (mAbs): mAbs rabbit anti-mouse conjugated with horseradish peroxidase for ITLC was obtained from Dako Corporation (Santa Barbara, Calif.); mAbs rabbit anti mouse IgM or IgG conjugated with horseradish peroxidase or alkaline phosphatase were obtained from Zymed (San Francisco, Calif.); mAb D.1.1. was kindly provided by Dr. David A. Cheresh (Scripps-Clinic, La Jolla, CA, ref. 5); mAb ME 311 was provided by Dr. Jan Thurin (The Wistar Institute, Philadelphia, Pa., ref. 6) and Jones antibody was provided by Dr. Andrew S. Blum (Rockefeller University, New York, N.Y., ref. 22). mAbs R 24, C5 and K9 were generated in our laboratory (23).

Synthesis of 0-acetyl-GD3 derivatives: GD3 was 0-acetylated slightly modified according to Haverkamp, et al. (24). 10 mg GD3, well dried, were dissolved in 250 μl pyridine (water free) in a small reaction vessel and incubated at 50° C. After 30 min. 150 μl N-acetyl-imidazole in pyridine (10 μg/μl) were added and the mixture was incubated at 50.C. At different time intervals, aliquots were taken and monitored by TLC and by analytical HPLC. Usually after 70h, more than 90% of GD3 was converted and the reaction was stopped by evaporating under a stream of nitrogen. Toluene was added during evaporation to remove remainig pyridine.

High Performance Thin Layer Chromatography (HPTLC): TLC-analysis was performed on HPTLC silica gel plates, whereby gangliosides and ganglioside-derivatives were run in solvent system chloroform/methanol/0.2% aqueous $CaCl_2$ 60:35:8 (v/v), neutral glycosphingolipids in solvent system chloroform/methanol/water 65:25:4 (v/v), ceramides in chloroform/methanol 95:5 (v/v) (25) and oligosaccharides in ethanol/n-butanol/pyridine/water/glacial acetic acid 100:10:10:30:3 (v/v) (26). Gangliosides, ganglioside derivatives and oligosaccacharides were visualized with orcinol/$H_2SO_4$ or resorcinol/HCl, neutral glycosphingolipids with orcinol/$H_2SO_4$ and ceramides in iodine vapor and Coomassie Blue (27).

High Performance Liquid Chromatography (HPLC): HPLC was performed using a Waters computer operated liquid chromatography system (Model 501). To monitor GD3 conversion and to estima approximate yields, analytical HPLC on a $NH_2$-column (3.9×300 mm) was performed as described by Gazzotti, et al. (28). For preparative separation $NH_2$-columns (21.4×250 mm) were used and aliquots of 5 mg ganglioside dissolved in destilled water were injected. The above mentioned method was modified as follows:

Buffer 1: acetonitrile/5mM phosphate 83:17 (v/v), pH 5.6; buffer 2: acetonitrile/20mM phosphate 1:1 (v/v), pH 5.6, programmed as follows: 30 min isocratic buffer 1/buffer 2 90:10 (v/v); 90 min. with a linear gradient from buffer 1/buffer 2 90:10 (v/v), to buffer 1/buffer 2 50:50 (v/v); 30 min isocratic buffer 1/buffer 2 50:50 (v/v) followed by 30 min buffer 2 100%; flow rate was 9 ml/min; eluting gangliosides were monitored at 205 nm in a flow-through detector. Fractions were pooled, dried on a rotary evaporator and re-chromatographed in the same system, followed by desalting on a C18-column (10×250 nm) using 200 ml water, 200 ml water/methanol 1:1 (v/v) and 200 ml methanol. Flow rate was 4 ml/min. Methanol fractions were dried and homogenicity was monitored by TLC.

Enzyme hydrolysis: 0-acetyl GD3 derivatives were treated with $V.$ cholerae sialidase (29), neutral cleavage products were separated by DEAE-Sephadex chromatography (30) and analyzed by TLC before and after base treatment with 0.05 M NaOH in methanol for 1 h at 37.C. In the case of sequential hydrolysis analysis, gangliosides were first cleaved by $V.$ cholerae sialidase; following purification by Sep-Pak C18 chromatography (31) and separation on DEAE Sephadex A 25 the neutral fractions were subsequently treated with μ-galactosidase. The reaction mixture contained 10–20 μg glycolipid, 0.1% sodium taurodeoxycholate dissolved in 0.05 M citric acid-sodium citrate buffer pH 4.0 and 0.1 U β-galactosidase (32). Incubation was carried out at 37° C. for 24 h. Following removal of sodium taurodeoxycholate by DEAE Sephadex A 25, aliquots of the cleaved glycolipids were analyzed by TLC before and after base treatmet in solvent system chloroform/methanol/water 65:25:4 (v/v).

Endoglycoceramidase treatment of 0-acetyl GD3 derivatives was performed according to Ito, et al. (25). Oligosaccharides and ceramides were analyzed by TLC before and after base treatment. Susceptability of 0-acetyl GD3 derivatives to cleavage by serum esterase activity was analyzed as follows: 20 μg GD3 or GD3 derivatives were incubated in the presence of 50 μl fresh human or mouse serum or in PBS containing 2% BSA for 24 h at 37° C. The glycolipids were re-extracted with chloroform/methanol/water 10:10:1 (v/v), purified by Sep-Pak C18 chromatography and analyzed by TLC and ITLC with mAbs R24 and D.1.1.

Reduction of the double bond in the ceramide portion of GD3 was performed with sodium borohydrid and palladiumchloride as catalyst (21).

Negative ion fast atom bombardment (FAB) mass spectrometry: Negative ion FAB mass spectra were recorded on a VG Analytical (model ZAB-SE) high resolution mass spectrometer (Manchester, England) equipped with a xenonion source. The FAB ion source was typically maintained at 8KV with 1 mA current. The sample was dissolved in a small amount of chloroform/methanol 2:1 (v/v) and an aliquoe containing about 10 μg of the sample was placed on the stainless steel sample holder. Thioglycerol, about 2 μl, was added as the matrix solvent before analysis.

High resolution nuclear magnetic resonance spectroscopy (NMR): For NMR analysis fraction F2 was further purified by Sephadex LH-20 chromatography, purged of exchangable protons by dissolving in DMSO-d6/D20 1:1 (v/v) and immediately lyophilized. The sample was then dissolved in DMSO-d6/D20 98:2 (v/v) containing traces of tetramethylsilane as internal standard. NMR spectra were obtained with a Bruker WM 500 spectrometer equipped with an Aspect 2000 computer operating in the Fourier transform mode as previously described (33).

Animals: Female BALB/c-057BL/6 F1-mice obtained from Jackson Laboratory (Bar Harbor, ME) 6 weeks of age were used for vaccination.

Vaccination: Mice were pretreated with cyclophosphamide at a dose of 15 mg/kg intraperitoneal 3 days before the first vaccine. Vaccines were prepared as follows: GD3 or GD3-derivatives prior dried down in conical tubes, were resuspended in dest. water containing *Salmonella minnesota* mutant R 595, prepared as described (15). The mixture was lyophilized and emulsified in PBS prior to vaccine administration. Groups of 10 mice, randomly selected, were immunized subcutaneously with given vaccine twice two weeks apart. Vaccines contained each 10 μg glycolipid and 0.5 mg *S. minesota* R 595 in a total volume of 100 μl PBS.

Mice were bled from the retro-orbital sinus before and two weeks after the first and second vaccine. Serum samples for serological testings were stored at −20° C. Sera were analyzed by dot plot assays, ELISA and ITLC. Dot plot immune stains were performed as previously described (34) modified as follows: 0.20 μg glycolipid was spotted on nitrocellulose stripes. The stripes were blocked for 1 h at room temperature in PBS containing 5% FCS, 1% BSA and 0.1% sodium acid and incubated with mouse serum (1:150) in small trays overnight at room temperature. After washing 5x in PBS containing 0.05% Tween 20, stripes were reacted with HRP-conjugated anti mouse IgM or IgG antibodies (1:200) for 5h at room temperature. Peroxidase staining was performed as described for ITLC. Stains were quantitated as negative, 1+, 2+ and 3+.

ELISA: 0.1 μg glycolipid in 50 μl ethanol was dried per well in a 96 well plate and blocked with PBS containing 3% BSA 2 h at 37 C. Wells were incubated with mouse sera serially diluted with PBS containing 3% BSA for 1h at room temperature. Plates were washed 5x with PBS containing 0.05% Tween 20 and incubated with AP-conjugated anti mouse IgM or IgG antibody (1:200) for 1 h at room temperature. After 5x washing with the above mentioned buffer, 100 μl phosphatase substrate solution (0.2% p-nitrophenyl phosphate disodium in PBS containing 3% BSA) was added to each well. After 30 min absorbance of the reaction product was measured at 414 nm. To eliminate the effect of unspecific "sticky" sera, sera was also tested on plates which had been processed identically but to which no glycolipid had been added. The optic densities at each titer obtained on these plates was substracted from the experimental value, yielding a corrected optic density.

ITLC: Immunostaining of gangliosides and ganglioside derivatives with monoclonal antibodies or mouse sera after separation on HPTLC silica gel glass plates was performed slightly modified according to Magnani (35) as previously described (36).

Serologic Response of Vaccinated Patients

Vaccination with BCG-ganglioside vaccines was well tolerated; all side effects detected were attributed to BCG. Vaccines resulted in low grade fever (less than 39° Centigrade) and prominent ulceration or inflammation at vaccine sites, requiring a decrease in the BCG dose to $3 \times 10^6$ organisms in 65% of patients. No neurologic or other detectable abnormalities were seen. Skin tests for delayed hypersensitivity to the immunizing gangliosides and to recall antigens were performed. Most patients were reactive with at least one recall antigen, but none were reactive with the immunizing ganglioside.

Table 1 shows the results of ELISAs for antibodies against the four gangliosides in sera from normal individuals and unvaccinated and vaccinated melanoma patients. Spontaneous high titer antibodies (greater than 1/40) against GD2 and GD3 were not detected in sera from normal donors or untreated melanoma patients. One normal donor had a titer of 1/80 against GM2 and another a titer of 1/80 against 9-0 acetyl GD3. Both were confirmed to be specific in immune stains. Several low titer antibody responses were detected against GM2 and 9-0-acetyl GD3. These sera failed to react in dot blot immune stains, so the specificity of these antibodies could not be analyzed. The 44 patients immunized with Cy+BCG-GM2 represent a composite of 24 previously reported patients and 20 patients immunized more recently. Seventy-five per cent of patients produced a high titer GM2 antibody response (see Table 1). The four additional patients with anti-GM2 titers of 40 all gave clear reactions in immune stains, reacting with GM2 and no other gangliosides. Of the seven patients with titers of 20 or less, only three received the full series of vaccinations. Recurrent melanoma was detected in the other four patients during the course of immunization, requiring treatment with other modalities before the booster immunization could be administered. Hence 92% of patients receiving the full series of immunizations produced anti GM2 antibodies. High titer antibody responses against GD2 and GD3 were not seen in patients immunized with either GD2 or GD3, or the six patients immunized with three gangliosides. Four patients produced anti GD2 titers of 40, two of these showed specific anti GD2 reactivity in immune stains. 9-0-acetyl GD3 was highly immunogenic, producing high titer antibodies in all six patients immunized. Sequential antibody responses detected in ELISAs on 9-0-acetyl GD3 for these six patients is shown in FIG. 1. While three of the patients produced high titer antibody during the initial series of immunizations, all showed the highest titer after the fourth (booster) immunization, a result similar to that seen with immunization against GM2. Also as described for GM2, the high titer antibody response was short-lived, median duration 8 weeks.

TABLE 1
ANTIBODY TITERS (ELISA) OF NORMAL DONORS, UNTREATED MELANOMA PATIENTS AND MELANOMA PATIENTS AFTER IMMUNIZATION WITH PURIFIED GANGLIOSIDE VACCINES

| Treatment | Total No. Patients | Target | 0 | 20 | 40 | 80 | 160 | 320 |
|---|---|---|---|---|---|---|---|---|
| Untreated | 44 | GM2 | 37 | 4 | 2 | 1 | 0 | 0 |
| Normal Donors | 30 | GD2 | 29 | 1 | 0 | 0 | 0 | 0 |
| | 30 | GD3 | 30 | 0 | 0 | 0 | 0 | 0 |
| | 30 | 9-O-acetyl GD3 | 25 | 3 | 1 | 1 | 0 | 0 |
| Melanoma Patients | 48 | GM2 | 37 | 8 | 3 | 0 | 0 | 0 |
| | 30 | GD2 | 28 | 2 | 0 | 0 | 0 | 0 |
| | 30 | GD3 | 30 | 0 | 0 | 0 | 0 | 0 |
| | 30 | 9-O-acetyl GD3 | 22 | 5 | 3 | 0 | 0 | 0 |
| Vaccinated With | | | | | | | | |
| BCG-GM2 | 44 | GM2 | 4 | 3 | 4 | 14 | 11 | 8 |
| BCG-GD2 | 6 | GD2 | 2 | 2 | 2 | 0 | 0 | 0 |
| BCG-GD3 | 6 | GD3 | 4 | 2 | 0 | 0 | 0 | 0 |
| BCG-GM2 + GD2 + GD3 | 6 | GM2 | 1 | 1 | | 1 | 3 | 0 |
| BCG-GM2 + GD2 + GD3 | | GD2 | 1 | 3 | 2 | 0 | 0 | 0 |
| BCG-GM2 + GD2 + GD3 | | GD3 | 3 | 3 | 0 | 0 | 0 | 0 |
| BCG-9-O-acetyl GD3 | 6 | 9-O-acetyl GD3 | 0 | 0 | 0 | 1 | 1 | 4 |

*Results on GM2 of normal donors and untreated melanoma patients published previously - ref. 10, and of 24 of the 44 GM2 vaccinated patients - ref. 11.

Specificity Analysis of Reactive Sera

The specificity of GM2-reactive sera induced by Cy+BCG-GM2 has been analyzed in detail and reported previously. Reactivity is restricted to GM2 and N-glycolyl GM2. Analysis of sera from the additional twenty patients reported here by dot blot immune stains and inhibition assays confirms this finding. Reactivity was restricted to GM2 and N-glycolyl GM2 in all patients. Dot blot immune strains with post-immunization sera from patients receiving BCG/GD2 and BCG/GD3 vaccines showed a low level of reactivity against GD2 in the two patients immunized with GM2+GD2+GD3 and having GD2 titers by ELISA of 40. Reactivity was restricted to 9-0-acetyl GD3. Inhibition assays were used to look with greater precision for cross reactivity of these antibodies with GD3 and none was detected.

Immune Adherence Assay of 9-0 Acetyl GD3 Antibodies

In preliminary studies, reactivity against melanoma cells has been shown. The titers in six patients ranged from ⅛ to 1/64.

Figure 2:
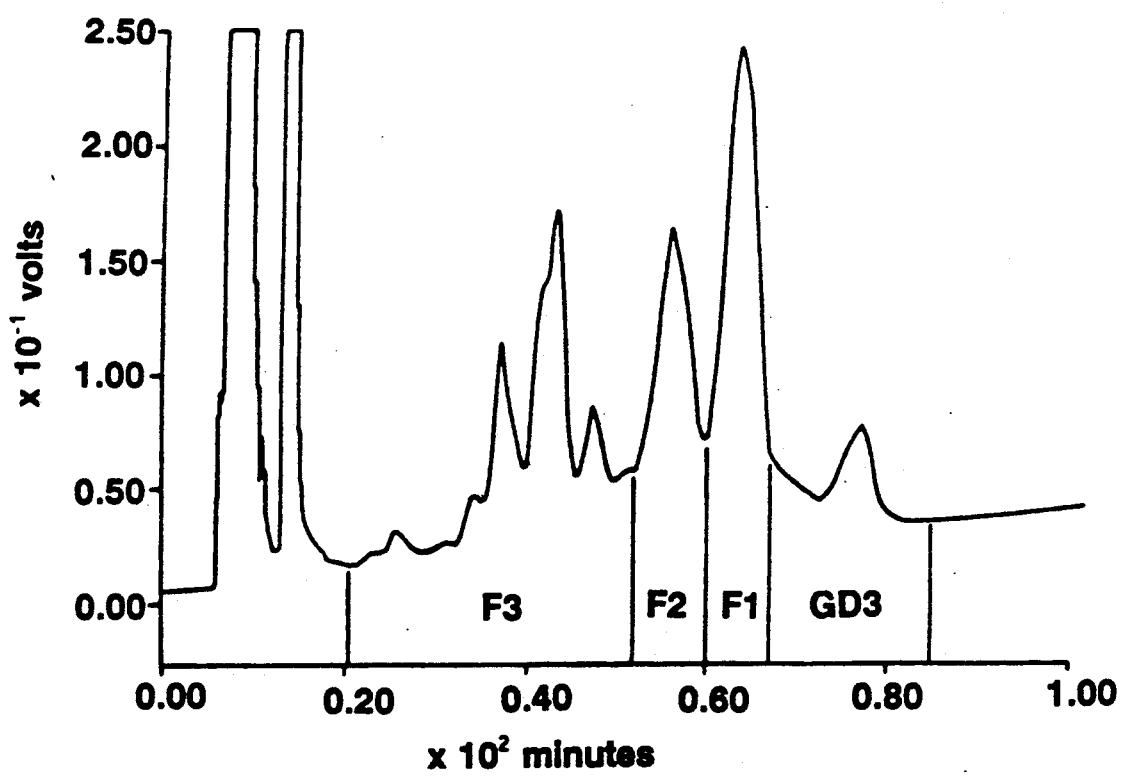
FIG. 2 shows the separation of 0-acetyl-GD3 derivatives by preparative HPLC. NH2-column (21.4×250 mm); buffer 1: acetonitrile/5mM phosphate 83:17 v/v; pH 5.6; buffer 2: acetonitrile/20mM phosphate 1:1 v/v; pH 5.6 programmed as follows: 30 min isocratic buffer 1/buffer 2 90:10 v/v; 90 min with a linear gradient from buffer 1/buffer 2 90:10 v/v to buffer 1/buffer 2 50:50 v/v; 30 min isocratic buffer 1/buffer 2 50:50 v/v; flow rate 9 ml/min; eluting gangliosides were monitored at 205 nm in a flow-through detector. F1-3 representing isolated fractions.

Preparation of the 0-acetyl derivative of GD3, F1, F2 and F3:

GD3 was 0-acetylated using N-acetyl-imidazole in pyridine. TLC-analysis, monitoring the process of acetylation, revealed that during the initial 30 h one major product was formed, migrating between GD3 and GM1, while the yield of higher migrating products remained low. After 70 h no further decrease of GD3, used as starting material, was observed and the ratio of all conversion products remained stable (FIG. 1). The conversion products were separated by preparative HPLC and pooled into 3 fractions referred to as F1, F2 and F3, respectively (FIG. 2). When the average ratio of the products (percent of total conversion products of four conversions) obtained from GD3 was estimated by densitometry after TLC separation or integration of the peak area obtained after analytical HPLC, F1 yielded 45 ±10%, F2 20±5%, F3 25±10% and GD3 10±7%.

Figure 3:
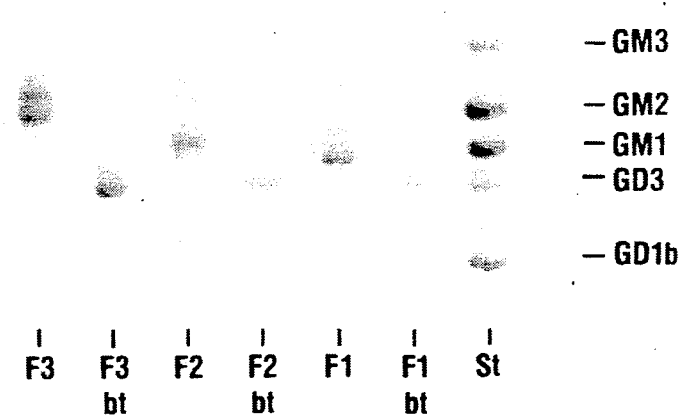
FIG. 3 shows the TLC-analysis of isolated 0-acetyl-GD3 derivatives F1, F2 and F3 before and after base treatment. bt referring to base treated fraction; HPTLC silica gel plate; running solvent: chloroform/methanol/0.2% aqueous CaCl$_2$ 60:35:8 v/v; spray reagent: orcinol/H$_2$SO$_4$.

Characterization of F1, F2 and F3:

The fractions obtained were characterized by TLC-analysis before and after base treatment (FIG. 3). Before base treatment, F1 migrated between GM1 and GD3, F2 ran slightly faster than GM1, and the 2 major bands of F3 migrated between GM2 and GM3. All fractions were sensitive to base treatement and were reconverted to a product co-migrating with the GD3, from which they were derived. Immune reactivity of the fractions with antiganglioside monoclonal antibodies was investigated by ITLC (Table 2).

Figure 4:
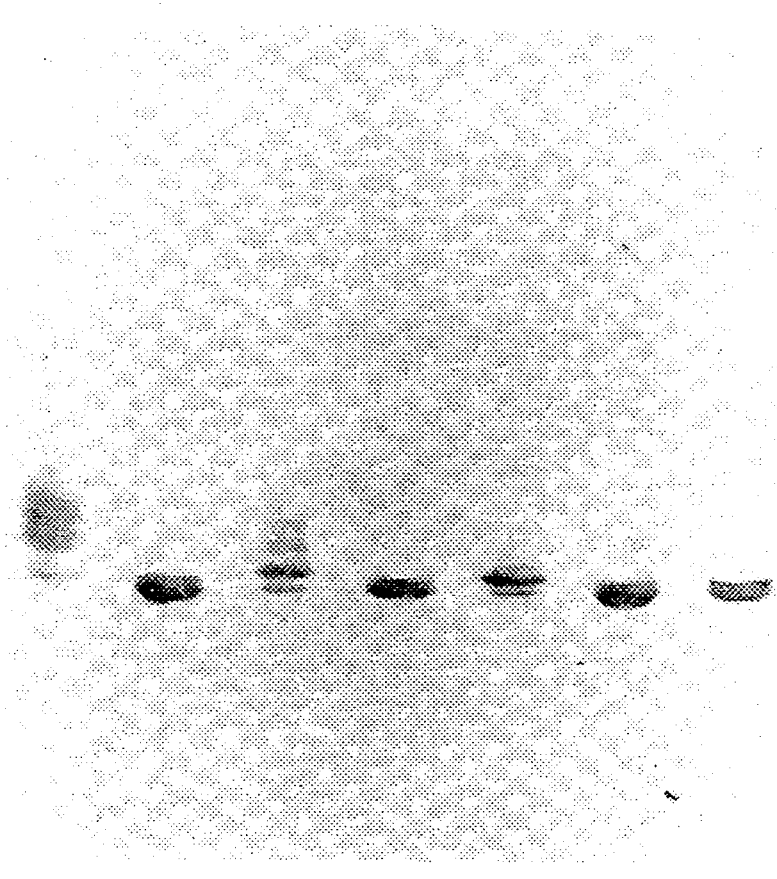
FIG. 4 shows the immune reactivity of TLC-separated 0-acetyl-GD3 derivatives F1, F2 and F3 before and after base treatment with mAbs R24 (recognizing GD3), D.1.1. and ME 311 (recognizing 9-0-acetyl GD3). HPTLC silica gel plate; running solvent: chloroform/methanol/0.2% aqueous CaCl$_2$ 60:35:8 v/v; detection: peroxidase and 4-chloro-1-naphthol staining.

GD3 and F1 showed reactivity only with anti GD3 antibodies, whereas F2 and F3 reacted with monoclonal antibodies against 9-0-acetyl GD3 as well as GD3. This reactivity with antibodies against 9-0-acetyl GD3 was lost after base treatment (FIG. 4).

Further information about the localization of the acetyl groups was obtained by TLC-analysis of oligosaccharides and ceramides after treatment with endoglycoceramidase. Base treated and non base treated ceramides from F1, F2 and F3 co-migrated with ceramide derived from native GD3. Comparing the conversion products of original GD3 and GD3, in which the double bond in the ceramide protion was reduced prior to acetylation differences in quality and quantity of the bands could not be observed by TLC analysis, also indicating that the acetylation site was not in the ceramide moiety. Oligosaccharides, however, showed different mobility, with relative migration rates similiar to that of their parent gangliosides and after base treatment they co-migrated with GD3-oligosaccharide, suggesting 0-acetylation on the oligosaccharide moiety of GD3.

TABLE 2
IMMUNOREACTIVITY OF O-ACETYL-GD3 DERIVATIVES*

| | MABS | | | | | |
|---|---|---|---|---|---|---|
| | anti-9-O-AcGD3 | | | anti-GD3 | | |
| DERIVATIVE | D.1.1[1] | ME 311[2] | JONES[3] | R24[4] | C5[4] | K9[4] |
| GD3 | − | − | − | + | + | + |
| F1 | − | − | − | + | + | + |
| F2 | + | + | + | + | + | + |

TABLE 2-continued

IMMUNOREACTIVITY OF O-ACETYL-GD3 DERIVATIVES*

| | MABS | | | | | |
|---|---|---|---|---|---|---|
| | anti-9-O-AcGD3 | | | anti-GD3 | | |
| DERIVATIVE | D.1.1[1] | ME 311[2] | JONES[3] | R24[4] | C5[4] | K9[4] |
| F3 | + | + | + | + | + | + |

([1]Cheresh, et al. 1984; [2]Thurin, et al. 1985; [3]Blun, et al. 1987; [4]Dippold, et al. 1980, *tested by ITLC)
Immune reactivity of O-acetyl-GD3 derivatives F1, F2 and F3 with anti ganglioside monoclonal antibodies as determined by ITLC. mAbs were incubated at 4° C. overnight; mAb dilutions: K9, C5 and R24 20 lg/ml; D.1.1. 1:500; Jones antibody 1:200; ME 311 supernatant 1:5; HRP-rabbit-anti-mouse 1:200.

Figure 5:
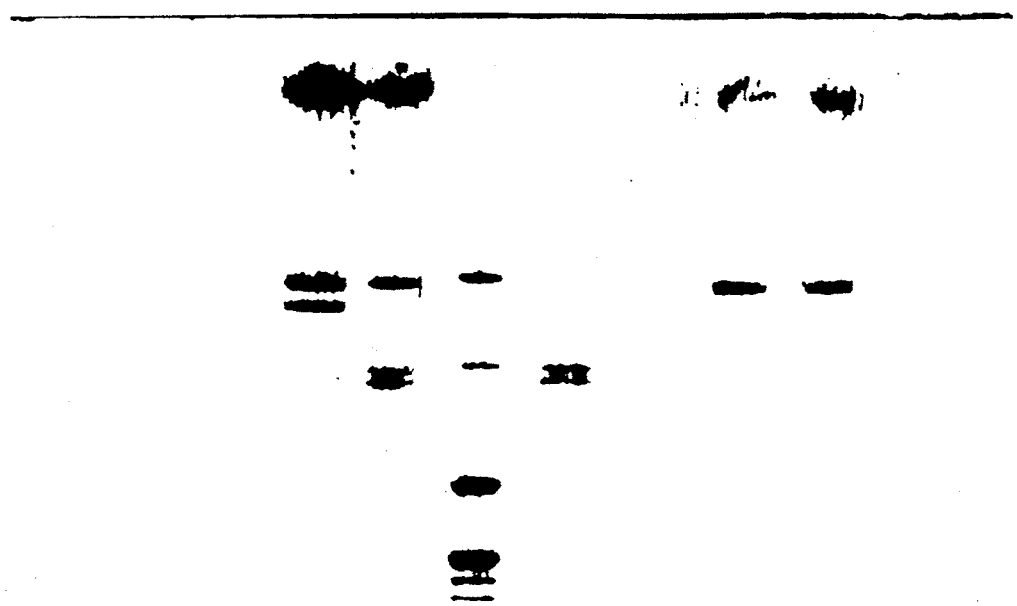
FIG. 5 shows the TLC-analysis of neutral core products obtained after exoglycosidase treatment of fraction F1. Lanes: 1, F1+sialidase; 2, F1+sialidase followed by base treatment; 3, F1+sialidase followed by $\beta$-galactosidase; 4, F1+sialidase +$\beta$-galactosidase followed by base treatment; 5, neutral glycosphingolipids derived from human spleen; 6, GD3 +sialidase; 7, GD3 +sialidase followed by base treatment; 8, GD3 +sialidase followed by $\beta$-galactosidase; 9, GD3 +sialidase +$\beta$-galactosidase followed by base treatment; HPTLC silica gel plate; running solvent: chloroform/methanol/water 65:25:4 v/v; spray reagent: orcinol/H$_2$SO$_4$.

TLC-analysis after treatment with *V. cholerae* sialidase revealed that the major hydrolysis product derived from F1 migrated between CMH and CDH, the majority of F2 comigrated with CDH derived from parent GD3, and the hydrolysis products of F3 co-migrated with CDH and the F1 hydrolysis product. Only bands co-migrating with CDH could be detected after base treatment. Sequential hydrolysis of fraction F1 first by sialidase followed by treatment with β-galactosidase and TLC analysis of the neutral cleavage products, before and after base treatment, resulted in the following: (FIG. 5). The neutral F1-hydrolysis product obtained after sialidase treatment, which migrated between CMH and CDH was resistant to β-galactosidase treatment, while the hydrolysis product co-migrating the CDH was completely converted to CMH.

Negative-ion fast atom bombardment mass spectroscopy of fraction F2 showed a highest peak of m/z 1554, corresponding to GD3 containing two acetyl-groups (!470 +42 +42). Fragments of m/z 1513 (GD3 +acetyl), m/z 1470 (GD3), m/z 641 (sialic acid +sialic acid +acetyl) and m/z 599 (sialic acid +sialic acid) could be detected indicating one acetylation site in the sialic acid portion of the GD3 molecule (FIG. 6A, 6B, and 6C).

Figure 7:
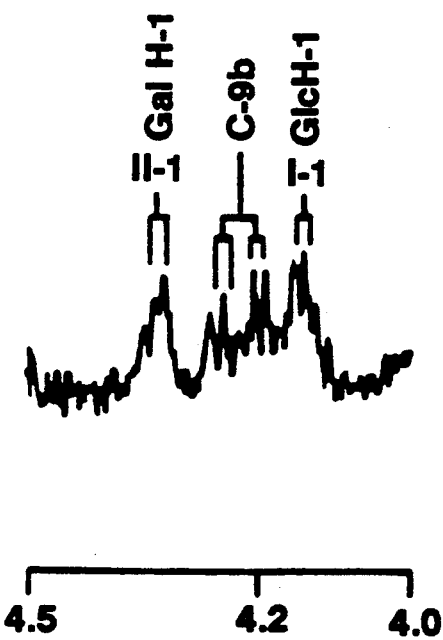
FIG. 7 shows the partial 490-MHz $^1$H NMR spectrum of fraction F2 in DMSO-d6/D20 at 303° K. (4.5–4.2 ppm) showing the chemical shifts between II-1 and I-1 characteristic for 9-0-acetylation of sialic acids.

This fraction was further analyzed by proton nuclear magnetic resonance spectroscopy to pin point the exact position of the 0-acetylation site. The NMR spectrum of fraction F2 revealed typical chemical shifts in the range of 4.2 ppm which can not be detected in original GD3, indicating 0-acetylation in position C9 of the sialic acid portion of GD3 (FIG. 7).

These observations suggest that fraction F1 was 0-acetylated on the lactose core of the ganglioside, fraction F2 contains two 0-acetyl groups and was 0-acetylated in position C-9 of the sialic acid moiety and fraction F3 was probably poly-0-acetylated, containing various epitopes recognized by 9-0-acetyl GD3 specific antibodies.

Susceptibility of F1, F2 and F3 to cleavage by serum esterases:

Because immunization of melanoma patients with these 0-acetyl GD3 derivatives was contemplated, it was important to determine whether they were resistant or susceptable to cleavage by serum esterases. After in vitro exposure to fresh human serum for 24 h at 37° C., followed by re-extraction, TLC-separation and chemical or immuno staining, all 0-acetylated GD3 derivatives were recovered.

Immunogenicity of F1, F2 and F3 in mice:

Table 3 shows the results of vaccination studies.

TABLE 3

| VACCINE | NO. OF MICE | TARGET | ELISA TITERS IgM | ELISA TITERS IgG | DOT BLOT IMMUNE STAIN |
|---|---|---|---|---|---|
| GD3 | 10 | GD3 | 40(2), 20(8) | — | |
| | | F1 | — | | (2) |
| | | F2 | — | | |
| | | F3 | — | | |
| F1 | 10 | GD3 | 80, 40, 20(4) | — | (3) |
| | | F1 | 160, 40, 20(5) | — | (4) |
| | | F2 | 80, 20(6) | — | (4) |
| | | F3 | | | (2) |
| F2 | 10 | GD3 | 80, 40(4), 20(5) | — | |
| | | F1 | | | (3) |
| | | F2 | 80(2), 40(7), 20 | — | (9) |
| | | F3 | 80, 40(5), 20(2) | — | (9) |
| F3 | 10 | GD3 | 40(2), 20(4) | — | (1) |
| | | F1 | | | (1) |
| | | F2 | 320(2), 160(3), 40(3), 20(1) | 1280(3), 660(2), 80(1) | |
| | | F3 | 1280(2), 640(3), 160(3), 80(2) | 1280(2), 640(3), 320, 160(2), 40, 20 | |

DISCUSSION

We have studied sera and monoclonal antibodies derived from melanoma patients to identify melanoma cell surface antigens that are immunogenic in man (37-39). Since reactivity against melanoma antigens was found in only a small percentage of patients, we have attempted to induce antibodies using vaccines containing irradiated cells expressing them. While we have detected reactivity against a variety of antigens in these studies, reactions against gangliosides have been predominant (10-12). These have included serum antibodies against GM2 and GD2 and human monoclonal antibodies against GM2, GM3, GD2, GD3 and X. Likewise Tai et al. have reported that antibodies against GM2 were induced in 10 of 26 patients receiving irradiated whole melanoma cell vaccines and that antibodies against GD2 wer detected in 2 patients (13). In a previous study, we used the immunization approach found most active in initial preclinical and clinical trials, Cy pretreatment to decrease suppressor activity and immunization with BCG conjugated to purified GM2 ganglioside. High titer antibody against GM2 was induced in 17 of 24 patients entered, 17 of 21 patients receiving the full course of immunizations. Since GM3 and GD3 are the most abundantly expressed gangliosides on most melanoma cells and no antibodies against these two have been detected, it has been assumed that they are not immunogenic. Nothing was known about the immunogenicity of 9-0-acetyl GD3. While Ravindranaths et al. have recently described 2 melanoma patients with antibody reactivity against 9-0-acetyl and/or 4-0 acetyl GD3, the incidence of such antibodies in melanoma patients was unknown (18). No antibodies against 9-0-acetyl GD3 have been reported in patients receiving whole cell melanoma vaccines, but this may reflect lack of 9-0-acetyl GD3 on the immunizing cells or the target cells for serological assays, rather than poor immunogenicity. We have recently shown that the immunogenicity of a series of gangliosides in the mouse as well as in man was inversely proportional to their expression on normal tissues. The low expression of 9-0-acetyl GD3 on normal tissues in man suggested it might be immunogenic. Since Cy +BCG-GM2 was more effective than the immunization approaches used previously, we were eager to apply it to induction of antibodies against GD2, GD3 and 9-0-acetyl GD3. We show here that 9-0-acetyl GD3 is highly immunogenic, as immunogenic as GM2, and that using this approach, GD2 is only slightly immunogenic and GD3 is not immunogenic at all.

9-0 acetyl GD3 was originally identified as a melanoma antigen by Cheresh et al. using the mouse monoclonal antibody D1.1 established by Stallcup (5, 17). These reports and a subsequent one by Thurin et al. have shown the distribution of 9-0-acetyl GD3 to be largely restricted to melanoma cells. No expression on normal tissues was detected. While in depth immunohistologic studies have not yet been reported, the distribution pattern on normal tissues of 9-0-acetyl GD3 is less than GD2 or GD3 and appears to be comparable to or more restricted than GM2. In addition, Tchuda et al. have reported that 9-0-acetyl GD3 is expressed on all melanoma cells, generally in amounts comparable to GM2 (2). These factors and our studies in the mouse suggesting immunogenicity would be inversely proportional to expression on normal tissues lead us to acetylate GD3, isolate fractions containing 9-0 acetyl GD3 and confirm the immunogenicity of these fractions in mice. The 9-0-acetyl GD3 fraction utilized here has been shown by NMR to contain GD3 acetylated on the 9 position of the second sialic acid and a second acetyl group on the lactose backbone. Compared to GD3, no additional acetyl groups or other differences were detected. This fraction is completely converted to GD3 by base treatment and appears identical to the 9-0-acetyl GD3 identified on melanoma cells by Thurin. It reacts with 9-0-acetyl GD3 monoclonal antibodies D1.1, ME311 and Jones. Immunologic similarity of this fraction to that on melanoma cells is confirmed by the reactivity with melanoma cells of anti-9-0 acetyl GD3 antibodies induced in our patients. A second highly immunogenic melanoma ganglioside has been identified.

We have reported previously that patients developing GM2 antibody after vaccination have delayed melanoma recurrence (12). We have recently initiated a randomized study involving larger numbers of patients to determine whether the Cy+BCG-GM2 vaccine contributes to this apparent improvement in prognosis, or whether induction of GM2 antibody is merely a prognostic indicator. Expression of individual gangliosides on different cells in the same biopsy as well as in different biopsies varies considerably. Antigenic heterogeneity and the prospect that antibodies against different gangliosides would be synergistic, provide strong motivation for development of a multivalent melanoma vaccine. We show here that antibody induced in melanoma patients against GM2 and 9-0-acetyl GD3 are indeed synergistic, resulting in significant melanoma cell death in settings where neither alone were effective. Antibodies against GD3 would be expected to be especially potent, alone or in combination with these other antibodies, as GD3 expression on melanoma cells is generally 10-20-fold greater than that of GM2 or 9-0-acetyl GD3. Consequently, we have begun to explore approaches for increasing the immunogenicity of GD3.

References

1. Portoukalian, J., Zwingelstein, G., and Dore, J-F. Lipid composition of human malignant melanoma tumors at various levels of malignant growth. Eur. J. Biochem 94:19-23, 1979.
2. Tsuchida, T., Saxton, R. E., Morton, D. L. et al. Gangliosides of human melanoma. JNCI 78:45-54, 1987.
3. Natoli, E. J. Jr., Livingston, P. O., Cordon-Cardo, C., Pukel, C. S., Lloyd, K. O., Wiegandt, H., Szalay, J., Oettgen, H. F. and Old, L. J. A murine monoclonal antibody detecting N-acetyl and N-glycolyl GM2: Characterization of cell surface reactivity. Cancer Res. 46:4116-4120, 1986.
4. Real, F. X., Houghton, A. N., Albino, A. P., Cordon-Cardo, C., Melamed, M., Oettgen, H. F. and Old, L. J. Surface antigens of melanomas and melanocytes defined by mouse monoclonal antibodies: specificity analysis and comparison of antigen expression in cultured cells and tissues. Cancer Res. 45:4401-4411, 1985.
5. Cheresh, D. A., Varki, A. P., Varki, N. M., Stallcup, W. B., Levine, J. and Reisfeld, R. A. A monoclonal antibody recognizes an O-acylated sialic acid in a human melanoma-associated ganglioside. J. Biol. Chem. 12:7453-7459, 1984.
6. Thurin, J., Herlyn, M., Hindsgaul, O., Stromberg, N., Karlsson, K-A., Elder, D., Steplewski, Z. and Koprowski, H. Proton NMR and fast-atom bombardment mass spectrometry analysis of the melanoma-associated ganglioside 9-0-acetyl-GD3. J. Biol. Chem. 260:14-556-14-563, 1985.
7. Houghton, A. N., Mintzer, D., Cordon-Cardo, C., Welt, S., Fliegel, B., Vadhan, S., Carswell E., Melamed, M. R., Oettgen, H. F. and Old, L. J. Mouse monoclonal IgG3 antibody detecting GD3 ganglioside: a phase I trial in patients with malignant melanoma. Proc. Natl. Acad. Sci. USA 82:1242, 1985.
8. Cheung, N-K. V., Lazarus, H., Miraldi, F. D., Abramowsky, C. R., Kallick, S., Saarinen, U. M., Spitzer, T., Strandjord, S. E., Coccia, P. F. and Berger, N. A. Ganglioside GD2 specific monoclonal antibody 3F8: a phase I study in patients with neuroblastoma and malignant melanoma. J. Clin. Oncol. 5:1430-1440, 1987.
9. Irie, R. F. and Morton, D. L. Regression of cutaneous metastatic melanoma by intralesional injection with human monoclonal antibody to ganglioside GD2. Proc. Natl. Acad. Sci. USA 83:8694-8698, 1986.
10. Livingston, P. O., Watanabe, T., Shiku, H., Houghton, A. N., Albino, A., Takahashi, T., Resnick, L. A., Michitsch, R., Pinsky, C. M., Oettgen, H. F. and Old, L. J. Serological response of melanoma patients receiving melanoma cell vaccines. I. autologous cultured melanoma cells. Int. J. Cancer 30:413-422, 1982.
11. Livingston, P. O., Takeyama, H., Pollack, M. S., Houghton, A. N., Albino, A., Pinsky, C. M., Oettgen, H. F. and Old, L. J. Serological responses of melanoma patients to vaccines derived from allogeneic cultured melanoma cells. Int. J. Cancer 31:567–575, 1983.

12. Livingston, P.O., Natoli, E. J. Jr., Jones Calves, M., Stockert, E., Oettgen, H. F. and Old, L. J. Vaccines containing purified GM2 ganglioside elicit GM2 antibodies in melanoma patients. Proc. Natl. Acad. Sci USA 84:2911–2915, 1987.

13. Tai, T., Cahan, L. D., Tsuchida, T., et al. Immunogenicity of melanoma-associated gangliosides in cancer patients. Int. J. Cancer 35:607–612, 1985.

14. Livingston, P.O., Jones, M., Deleo, A. B., Oettgen, H. F. and Old, L. J. The serological response to Meth A sarcoma vaccines after Cyclophosphamide treatment is further increased by various adjuvants. J. Immunol. 135:1505–1509, 1985.

15. Livingston, P.O., Joens Calves, M. and Natoli, E. J. Jr. Approaches to augmenting the immunogenicity of the ganglioside GM2 in mice: Purified GM2 is superior to whole cells. J. Immunol. 138:1524–1529, 1987.

16. Tsuchida, T., R. E. Saxton, and R. F. Irie. 1987. Gangliosides of human melanoma: GM2 and tumorigenicity. J. Natl. Cancer Inst., 78: 55–59.

17. Cheresh, D. A. and Reisfeld, R. A. 0-acetylation of disialoganglioside GD3 by human melanoma cells create a unique antigenic determinant. Science 225:844–846, 1984.

18. Ravindranaths, M. H., Paulson, J. C. and Irie, R. F. Human melanoma antigen 0-acetylated ganglioside GD3 is recognized by Cancer antennarius Lectin. J Biol. Chem. 263:2079–2086, 1988.

19. Cahan, L. D., Irie, R. F., Singh, R., Cassidenti, A. and Paulson, J. C. Identification of a human neuroectodermal tumor antigen. (OFA-I-2) as ganglioside GD2. Proc. Natl. Acad. Sci. USA 79:7629, 1982.

20. Pinsky, C. M., El Domeiri, A., Caron, A. S., Knapper, W. H. and Oettgen, H. F. Delayed hypersensitivity reactions in patients with cancer. Rec. Results Cancer Res. 47:37–41, 1974.

21. Blum, A. S., and C. J. Barnstable. 1987. 0-Acetylation of a cell-surface carbohydrate creates discrete molecular patterns during neural development. Proc. Natl. Acad. Sci. USA. 84: 8716–8720.

22. Dippold, W. G., K.O. Lloyd, L. T. Li, H. Ikeda, H. F. Oettgen, and L. J. Old. 1980. Cell surface antigens of human malignant melanoma: definition of six antigenic systems with monoclonal antibodies. Proc. Natl. Acad. Sci. USA. 77: 6114–6118.

23. Haverkamp, J., R. Schauer, M. Wember, J. P. Kamerling, and J. F. G. Vliegenthart. 1975. Synthesis of 9-0-acetyl- and 4,9-di-0-acetyl derivatives of the methyl ester of N-acetyl- -D-neuraminic acid methylglycoside. Hoppe-Seyler's Z. Physiol. Chem. 356: 1575–1583.

24. Ito, M., and T. Yamagata. 1986. A novel glycosphingolipid-degrading enzyme cleaves of the linkage between the oligosacaride and ceramide of neutral and acidic glycosphingolipids. J. Biol. Chem. 262: 14–278-14–282.

25. Veh, R. W., J.-C. Michalski, A. P. Corfield, M. Sander-Wewer, D. Gies, and R. Schauer. 1981. New chromatographic system for the rapid analysis and preparation of colostrum sialooligosaccharides. J. Chromatogr. 212: 313–322.

26. Nakamura, K., and S. Handa. 1984. Coomassie brilliant blue staining of lipids on thin-layer plates. Anal. Biochem. 142: 406–410.

27. Gazzotti, G., S. Sonnino, and R. Ghidoni. 1985. Normal-phase high-performance liquid chromatographic separation of non-derivatized ganglioside mixtures. J. Chromatogr. 348: 371–378.

28. Schauer, R. 1978. Characterization of sialic acids. In: V. Ginsburg (ed.), Methods in enzymology, Vol. L., part C: 64–89.

29. Ledeen, R. W., R. K. Yu, and L. F. Eng. 1973. Gangliosides of human myelin sialogalactosylceramide as a major component. J. Neurochem. 21: 829–839.

30. Kubo, H., and M. Hoshi. 1985. Elimination of silica gel from gangliosides by using a reversed-phase column after preparative thin-layer chromatography. J. Lipid Res. 26: 638–641.

31. Li, S. C., Mazzotta, M. Y., and Li, Y. T. (1975). Isolation and characterization of jack bean $\beta$-galactosidase. J. Biol. Chem. 250: 6786–6791.

32. Momoi, T., and Wiegandt, H. (1980). Separation and micro-detection of oligosaccharides of glycosophingolipids by high performance cellulose thin-layer chromatography-autoradiofluorography. Hoppe-Seyler's Z. Physiol. Chem. 361: 1201–1210.

33. Yu, R. K., T. A. W. Koerner, S. Ando., H. C. Yohe, and J. H. Prestegard. 1985. High-resolution proton NMR studies of gangliosides. III. Elucidation of the structure of GM3 lactone. J. Biochem. 98: 1367–1373.

34. Towbin, H., Schoenenberger, C., Ball, R., Braun, D. G., and Rosenfelder, G. (1984). Glycosphingo-lipid-blotting: an immunological detection procedure after separation by thin layer chromatography J. Immunol. Meth. 72: 471–479.

35. Magnani, J. L., D. F. Smith, and V. Ginsburg. 1980. Detection of gangliosides that bind cholera toxin: direct binding of $^{125}$I-labeled toxin to thin-layer chromatograms. Anal. Biochem. 109:399.

36. Ritter, G., W. Krause, R. Geyer, S. Stirm, and H. Wiegandt. 1987. Glycosphingolipid composition of human semen. Arch. Biochem. Biophys. 257: 370–378.

37. Old, L. J. Cancer immunology: The search for specificity—G. H. A. Cloves Memorial Lecture. Cancer Res. 41:361–375, 1981.

38. Houghton, A. N., Brooks, H., Cote, R. J., Taormina, M. C., Oettgen, H. F. and Old, L. J. Detection of cell surface and intracellular antigens by human monoclonal antibodies. J. Exp. Med. 158:53–65, 1983.

39. Yamaguchi, H., Furukawa, K., Fortunato, S. R., Livingston, P.O, Lloyd, K.O., Oettgen, H. F. and Old, L. J. Cell-surface antigens of melanoma recognized by human monoclonal antibodies. Immunology 84:2416–2420, 1987.

What is claimed is:

1. A composition for stimulating or enhancing in a subject to whom the composition is administered, production of antibodies against 9-O-acetyl GD3 ganglioside comprising an amount of a 9-O-acetyl GD3 ganglioside effective to stimulate or enhance antibody production in the subject and a pharmaceutically acceptable carrier.

2. A composition of claim 1 which additionally comprises an adjuvant.

3. A composition of claim 2, wherein the adjuvant is a microbial adjuvant.

4. A composition of claim 3, wherein the microbial adjuvant comprises *Salmonella minnesota* R595.

5. A composition of claim 3, wherein the microbial adjuvant comprises bacillus Calmette-Guerin.

6. A composition of claim 1, wherein the effective amount of 9-O-acetyl GD3 ganglioside comprises an amount between about 50 micrograms and about 300 micrograms.

7. A composition of claim 1, wherein the 9-O-acetyl GD3 ganglioside is purified from a biological source.

8. A composition of claim 7, wherein the biological source is a melanoma cell.

9. A composition of claim 7, wherein the biological source is milk.

10. A composition of claim 7, wherein the biological source is buttermilk.

11. A composition of claim 1, whick additionally comprises purified GM2 ganglioside.

12. A method for stimulating or enhancing in a subject production of antibodies against 9-O-acetyl GD3 ganglioside comprising administering to the subject an effective dose of a composition of claim 1.

13. A method of claim 12, wherein the 9-O-acetyl GD3 ganglioside is bound to a microbial adjuvant.

14. A method of claim 12, wherein the 9-O-acetyl GD3 ganglioside is bound to the microbial adjuvant by a hydrophobic bond between the lipid portion of the 9-O-acetyl GD3 ganglioside and the cell membrane of the microbial adjuvant.

15. A method of claim 12, wherein the microbial adjuvant is *Salmonella minnesota* R595 or bacillus Calmette-Guerin.

16. A method of claim 12, wherein an effective amount of cyclophosphamide is administered to the subject prior to administering the composition.

17. A method of claim 16, wherein the cyclophosphamide is administered between about 3 days and about 7 days prior to the administering the composition.

18. A method of claim 16, wherein the effective amount of cyclophosphamide is between about 1 $mg/m^2$ and about 500 $mg/m^2$.

19. A 9-O-acetyl GD3 ganglioside designated F2 characterized by the presence of a second acetyl group and the mass spectra shown in FIGS. 6A, 6B, and 6C.

20. A 9-O-acetyl GD3 ganglioside designated F3 characterized by the presence of 2 or more additional acetyl groups and recoverable from a mixture of acetylated derivatives of GD3 by a high pressure liquid chromatography.

21. A mixture of the 9-O-acetyl GD3 gangliosides F2 and F3.

22. A composition for stimulating or enhancing in a subject to whom the composition is administered, production of antibodies against 9-O-acetyl GD3 ganglioside comprising an amount of a 9-O-acetyl GD3 ganglioside of any of claims 38, 39 or 40 effective to stimulate or enhance antibody production in the subject and a pharmaceutically acceptable carrier.

* * * * *